United States Patent [19]

Nowak et al.

[11] 4,112,244
[45] Sep. 5, 1978

[54] RECOVERY OF HYDROQUINONE

[75] Inventors: Edward Norbert Nowak, Uniontown; William Shepherd Hollingshead, Cuyahoga Falls, both of Ohio

[73] Assignee: The Goodyear Tire & Rubber Company, Akron, Ohio

[21] Appl. No.: 870,051

[22] Filed: Jan. 16, 1978

[51] Int. Cl.$^2$ ............................................. C07C 37/08
[52] U.S. Cl. .................................................. 568/768
[58] Field of Search ................. 260/621 A, 621 C, 625

[56] References Cited

U.S. PATENT DOCUMENTS

| | | | |
|---|---|---|---|
| 3,798,277 | 3/1974 | Sugiyama | 260/621 C |
| 3,968,723 | 7/1976 | Burkholder et al. | 260/621 C |
| 4,049,723 | 9/1977 | Tanaha et al. | 260/621 C |

Primary Examiner—James O. Thomas, Jr.
Assistant Examiner—Werren B. Lone
Attorney, Agent, or Firm—D. B. Little

[57] ABSTRACT

Hydroquinone is obtained in greater than 95 percent yield through a nonaqueous recovery process compatible with the methyl isobutyl ketone (MIBK) based diisopropylbenzene dihydroperoxide isolation process. Hydroquinone, from the Hock-splitting reaction, is precipitated (after most of the reaction solvent is distilled off), separated, repulped in acetone, crystallized and separated again. The supernatant from the first separation step contains hydroquinone along with tars. This stream is subjected to a purification process comprising a series of distillation and extraction steps so that the hydroquinone in that stream can be recycled back into the process.

9 Claims, 1 Drawing Figure

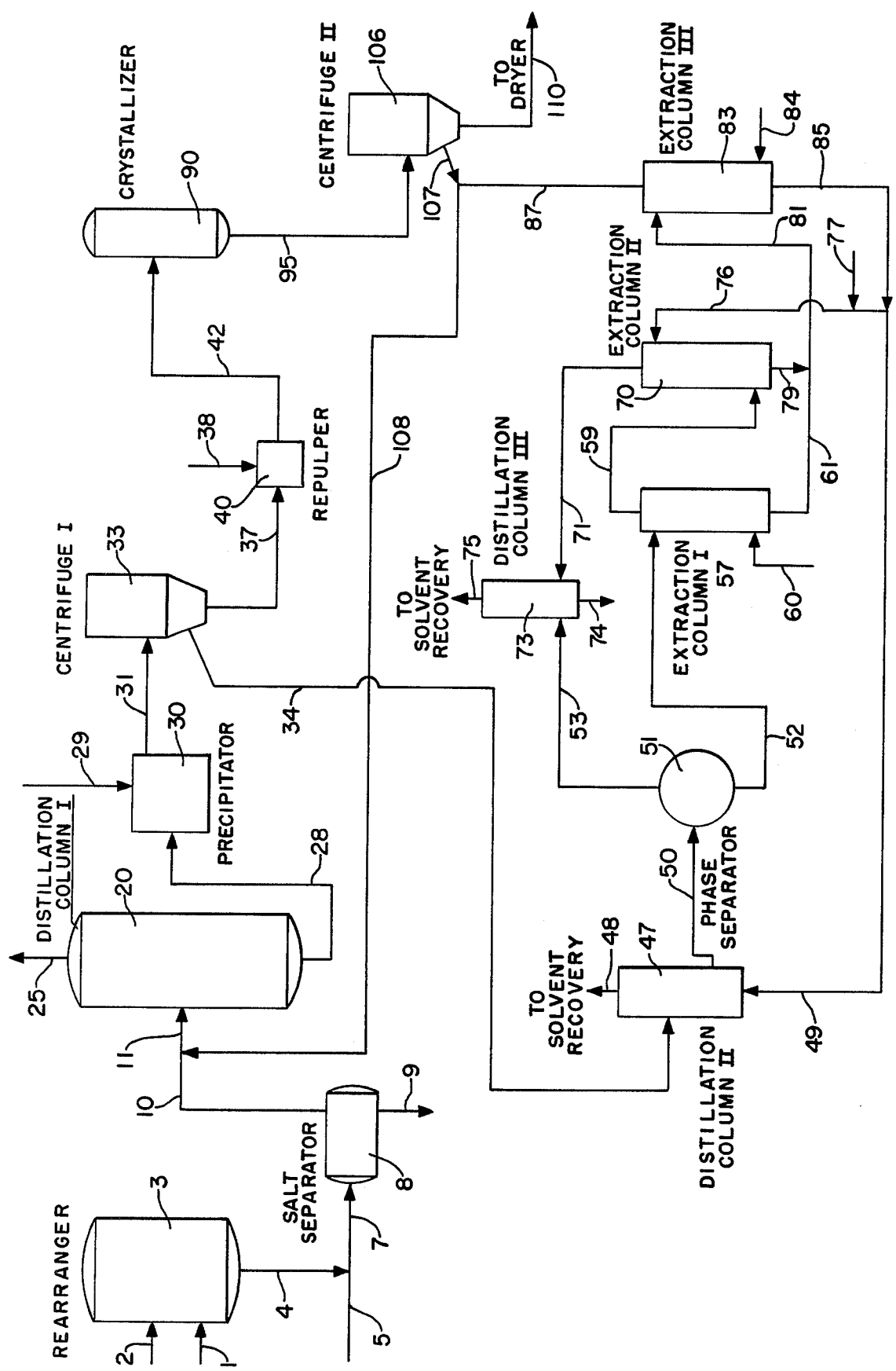

RECOVERY OF HYDROQUINONE

BACKGROUND OF THE INVENTION

The field of this invention is the synthesis of hydroquinone by acid cleavage (Hock-splitting) and recovery of hydroquinone from the reactor effluent.

The acid catalyzed cleavage or rearrangement of isopropylbenzene hydroperoxide was shown by Hock and Lang, Ber. 77B, p. 257 (1955), thus the name Hock-splitting. This reaction has been developed and used in the manufacture of phenolic compounds, including hydroquinone by the cleavage of p-diisopropylbenzene dihydroperoxide.

There has been a continuing effort on the part of those working in the field to develop a process which has a high level of product purity. The reason for this is that hydroquinone must be a white crystal or crystalline powder which meets ASA specification PH 4.126–1962 in order to be photographic grade. A high standard for whiteness is imperative for photographic grade material. Hydroquinone is used widely as the main ingredient in black and white film print developing.

Hydroquinone is also useful as a polymerization inhibitor and as an antioxidant. Hydroquinone itself and derivatives, such as 2,5-di-tert.-butylhydroquinone and butylated hydroxyanisole (BHA), are used for the prevention of oxidation in animal fat and aviation fuels.

By-products of the Hock-splitting (or rearrangement) reaction, referred to as tars, are believed to be the major impediment to high purity. Among the components of these tars are: p-isopropylphenol, α-hydroxy-p-isopropylphenol, p-diisopropylbenzene, p-isopropenylphenol, isopropenyl acetophenone, and dimers and trimers of the product and by-products. These impurities and by-products must be removed from the rearrangement product mixture in order to obtain a good color grade and high purity product.

Two processes applying the Hock-splitting reaction to p-diisopropylbenzene dihydroperoxide are found in the U.S. Pat. Nos. 3,884,983 and 3,968,171. These processes both employ benzene as a reaction solvent and as an extractant in removing tars.

Benzene has been the subject of regulatory action. The Occupational Safety and Health Administration has promulgated an emergency temporary standard bringing the average allowed exposure of a worker to benzene down to one part per million on a time-weighted basis, and allowing no more than five parts per million (ppm) peak exposure in factories during any 15-minute period. Even prior to this regulation the exposure was limited to 10 ppm. Thus, it is desirable to limit as much as possible the use of benzene in the process for making hydroquinone.

There are several processes, besides the two already mentioned, which use as the first five unit operations: rearrangement reaction, neutralization, removal of salts from the mixture, distillation and extraction to remove tars. In Japanese Pat. No. 69/017762, the extractant is an aromatic hydrocarbon such as benzene or toluene. U.S. Pat. No. 3,798,277 is a similar process except that its extractant is a halogenated hydrocarbon such as methylene chloride and alkyl ethers such as isopropylether, both of which are hazardous types of materials. Other extraction purification processes are found in Japanese Pat. Nos. 74/18835 (CA 81:13265n) and 74/18836 (CA-81:13264m).

A significant advance in the processing technology for phenolic compounds occurred when the process for isolating mono and dihydroperoxides by selective extraction first into a caustic solution, then into a water-insoluble organic liquid (exemplified by methyl isobutyl ketone) extractant was developed. This process has been described in Graham, World Petroleum Congress, proceedings, 7th, 1967 (Pub 1968), 5, 29–40 (Great Britain) and in U.S. Pat. Nos. 2,856,432; 2,856,433; 3,190,923; and 3,190,924. This process can be applied to the manufacture of p-diisopropylbenzene dihydroperoxide and insures that this material will enter the rearrangement reactor free of any benzene in the reaction solvent. It has the added benefit of a generally purer feed to the rearrangement reaction.

An application of the above methyl isobutyl ketone (MIBK) process to the manufacture of hydroquinone is described in Ewers, Voges, and Maleck, *Erdoel Kohle Erdgas Petrochem, Br. Chem.*, 28(1) 34+(1975, West Germany). In this process (hereinafter referred to by the name of the owner, Veba-Chemie A.G.) the MIBK extract containing p-diisopropylbenzene dihydroperoxide is distillatively dried and then subjected to the Hock-splitting reaction. Reactor effluent is subjected to neutralization, distillation to remove the acetone formed in the reaction and part of the MIBK reaction solvent, extraction of the distillation bottoms with water, extraction of the hydroquinone-bearing aqueous extract with MIBK to remove impurities, concentration of the purified aqueous extract, and crystallization of the hydroquinone. Parts of this process are described in German Offenlegungsschrift No. 2446992, Apr. 15, 1976.

A process for purifying hydroquinone by successive aqueous extractions of the tars is described in U.S. Pat. No. 3,900,523. In that process it is a steam distillation following the rearrangement reaction which removes the reaction solvent and forms a crude hydroquinone aqueous solution consisting essentially of water, hydroquinone, solvent and tar substances. The concentration of hydroquinone in this aqueous solution must be about 23 weight percent or more at a temperature of about 60° C.

The further purification of hydroquinone by recrystallization from acetone is described in Japanese Pat. Nos. 51039636 and 4872140 and German Offen. No. 2,541,489. In the German and the last mentioned Japanese documents the recrystallization is mentioned in connection with the MIBK process.

It is desirable to minimize or eliminate water from the hydroquinone purification because hydroquinone, in the presence of water (especially when heated) is subject to degradation to color bodies and polymeric material. Most of the aforementioned prior art patents are all aqueous processes. It has been found that advantages in product purity can be obtained if hydroquinone (formed in an MIBK-type solvent system by the Hock-splitting reaction) is maintained in a nonaqueous solvent system. A parallel process (involving a series of distillations and extractions) can be utilized to remove tars and separate and prepare hydroquinone carried with the tar-containing stream for recycle back to the main process equipment train. This combines the advantages of the MIBK process and extraction technology to keep water out of the main process stream.

SUMMARY OF THE INVENTION

Hydroquinone may be synthesized by the process steps of:

(A) reacting a feed stream comprising p-diisopropylbenzene dihydroperoxide in a reaction solvent selected from the group consisting of methyl isopropyl ketone, diisopropyl ketone, methyl isobutyl ketone, cyclohexanone, 1-pentanol, 3-pentanol, diethyl ether, diisopropyl ether, ethylisopropyl ether and mixtures of the foregoing with acetone with an acid catalyst to form hydroquinone and acetone;

(B) adjusting the pH of the mixture to from about 1.8 to 5.5 after the reaction by adding a base, thereby causing salts to form and precipitate;

(C) separating the precipitated salts from the supernatant mixture;

(D) feeding the supernatant mixture to a first distillation column in which most of the more volatile components are stripped out in the distillate and a concentrated hydroquinone stream is removed as tower bottoms; (E) precipitating hydroquinone crystals by adding a precipitating solvent to the bottoms stream from step (D);

(F) separating the hydroquinone crystals in the slurry obtained in step (E) from the supernatant organic liquid;

(G) feeding the supernatant liquid from step (F) to a second distillation column in which are combined the unit operations of distillation, to remove the acetone and most of the reaction solvent in the distillate and extraction of the hydroquinone into a water phase which exits the distillation column together with an organic phase as the distillation bottoms stream;

(H) subjecting the bottoms to a phase separation wherein the aqueous phase contains most of the hydroquinone and the organic phase contains substantially all the impurities and a small quantity of hydroquinone.

(I) extracting the aqueous phase from step (H) with an extractant selected from the group consisting of methyl isopropyl ketone, diisopropyl ketone, methyl isobutyl ketone, cyclohexanone, 1-pentanol, 3-pentanol, diethyl ether, diisopropyl ether, ethylisopropyl ether and mixtures of the foregoing in order to remove tars;

(J) extracting the organic extract from step (I) with water in order to recover residual hydroquinone from said extract;

(K) combining the aqueous raffinate from step (I) with the aqueous extract from step (J) and extracting the combined stream with an extractant selected from the group consisting of methyl isopropyl ketone, diisopropyl ketone, methyl isobutyl ketone, cyclohexanone, 1-pentanol, 3-pentanol, diethyl ether, diisopropyl ether, ethylisopropyl ether and mixtures of the foregoing; and (L) recycling the organic extract from step (K) to the distillation step (D).

A description of the rearrangement reaction (step A) can be found in U.S. Pat. No. 3,968,171, column 3, lines 31–44, which is hereby incorporated by reference into this application. For purposes of this process, the acid catalyst may be present in the range from 0.05 l to 3.0 weight percent of the reaction mixture. Water adversely affects the reaction by reducing acid strength and must be below 3 weight percent, preferably below 1 weight percent. The preferred temperature of the reaction is from 65° C. to 85° C.

The pH of the reaction effluent is preferably within the range of 3 to 4. Anhydrous ammonia gas is particularly effective as a neutralization agent because it is readily dispersible in the organic solution. Other bases which are useful are described in U.S. Pat. No. 3,927,124, column 2, lines 67–68 and column 3, lines 1–9, which is incorporated by reference into this application. That same patent describes a process for the pH adjustment or neutralization at column 3, lines 15–54 which is also incorporated by reference into this application. The pH adjustment may also be accomplished by simply mixing the base with the rearranger effluent.

The salt of the acid catalyst formed during the neutralization of pH adjustment step is insoluble in the reaction solvent and may thus be removed by precipitation, filtration or any other suitable solid liquid separation step. If precipitation is used, water is added to the reactor effluent prior to the salt separation step to facilitate the separation by dissolution of said salts into an aqueous phase which is withdrawn. However, separation means which do not involve the addition of water (such as filtration) are preferred.

The hydroquinone content of the supernatant stream from step (C) is generally from 1 to 15 weight percent, and is preferably from about 5 to 15 weight percent. In addition to the neutralized supernatant mixture, the first distillation column (step D) feed includes one other stream, containing extraction solvent, hydroquinone, and possibly acetone, precipitation solvent and impurities and minor constituents not critical to the present process.

The acetone obtained as a product of the rearrangement reaction and most of the reaction solvent are removed by distillation (step D) as overhead.

The bottoms from the distillation step (D) comprising principally hydroquinone, reaction solvent, and tars, is mixed with a precipitating solvent in which the tars and residual reaction solvent are soluble but which precipitates the hydroquinone as a crystalline product. The resultant two-phase stream is subjected to a solid/liquid separation step (F) such as centrifugation or filtration. The separated solid or slurry phase can be conveyed to a dryer for conventional handling thereafter.

The liquid supernatant or filtrate phase from step (F) is subjected to a purification process (steps G-L) in order to recycle the hydroquinone contained therein back to the first distillation step (D). Removal of color bodies from hydroquinone in the crude hydroquinone centrifuge filtrate is the heart of the recovery process. In the proposed process, advantage is taken of the difference between the distribution coefficients of hydroquinone and of the color bodies in a water/solvent system. The crude hydroquinone-containing supernatant from step (F) is combined with water and concentrated by distillation (step G). Both the reaction solvent and the precipitating solvent distill as their water azeotropes. The purpose of this operation is to reduce the volume of the organic solvents, particularly reaction solvent, thereby transferring hydroquinone to the aqueous phase. Step (G) has been operated at 88°–94° C. pot temperature and ambient pressure.

The tower bottoms stream from the second distillation comprises an organic phase comprising reaction solvent and precipitating solvent in which are dissolved the tars and some hydroquinone and a water phase in which is dissolved the hydroquinone to be recycled. The concentration of hydroquinone in this aqueous phase is about 5 to 25 weight percent, preferably 8 to 10 weight percent, and most preferably about 8 percent.

The aqueous phase is extracted with a minimal amount of MIBK in the first extraction step (I) to remove the remaining color bodies. Since this first MIBK extraction removes about one-third of the hydroquinone from the aqueous phase along with the color bodies, a back extaction to recover the hydroquinone is necessary. By using a volume of water several times that of the MIBK extract, the hydroquinone is back extracted in step (J) into water leaving the color bodies in the MIBK. It is desired to minimize hydroquinone in the extract from step (I) and in the raffinate from step (J). Preferred conditions to accomplish this are high extraction temperature, most preferably about 80° C. at atmospheric pressure.

The aqueous raffinate from step (I) and the aqueous extract from step (J) contain most of the hydroquinone which entered the recycle purification loop (steps G–L) but essentially free of tars. These streams are combined and extracted with reaction solvent in step (K) so that the hydroquinone recycled to the main process (step L) is also free of water. Step (K) is preferably carried out at low temperatures, most preferably about 25° C. at atmospheric pressure.

Recrystallization of the hydroquinone crystal slurry obtained in the precipitation step (E) renders a purer product via the following additional steps:

(M) repulping the crystals from step (F) in acetone;

(N) crystallizing the hydroquinone from the acetone; and (O) separating the hydroquinone crystals from the supernatant liquid. The liquid (mostly acetone) thus separated may be recycled to the distillation step (D).

The term "repulping" as used herein means dissolving a wet precipitate such as a filter cake or centrifuge cake in a solvent. The concentration of hydroquinone in the mixture leaving step (M) is generally between 30 and 50 weight percent. The purer the cake from step (F) is, the higher the concentration can be.

For obvious reasons of economy it is desirable to treat the tar-containing organic phase from the phase separation step (H) and the organic raffinate from step (J) to separate therefrom the valuable reaction solvent and precipitation solvent which they contain. This separation may be accomplished by combining the aforementioned streams and distilling off the solvents, in a tar removal column, which may be further purified and recycled into the process.

As a further economy, the water needed for steps (G) and (J) may be obtained by recycling the aqueous raffinate from step (K) with the addition of sufficient fresh water to make the material flows balance.

BRIEF DESCRIPTION OF THE DRAWING

The single FIGURE is a diagrammatic representation of the process of the present invention.

DESCRIPTION OF THE PREFERRED EMBODIMENTS

In the recommended nonaqueous process:

Reaction step (A)

Methyl isobutyl ketone is the reaction solvent and the extractant in steps (I) and (K). The feed to the reactor (step A) comprises a solution of about 20–22 weight percent diisopropylbenzene dihydroperoxide in MIBK containing about 10 weight percent acetone (to increase the solubility of the dihydroperoxide). Sulfuric acid is the reaction catalyst. Reaction temperature ranges from about 65° to about 70° C., and less than one weight percent water is present in the reaction mixture.

First Distillation Step (D)

Concentration of hydroquinone in the bottoms stream from the first distillation step (D) is generally 30–45 weight percent, preferably about 38%.

Precipitation Step (E)

The precipitating solvent of step (E) is xylene. The mixture in the precipitator is cooled by means of an external heat exchanger or by using a jacketed vessel, with cooling medium in the jacket, as the precipitator. The temperature of the mixture is maintained at from about −20° to about 40° C., preferably 20° to 30° C.

Although any weight ratio of xylene to distillation bottoms stream ranging from 0.1 to 1.5 may be used, a ratio of about 0.6 is preferred.

The rate of addition of xylene and the rate of cooling govern the crystal habit of the hydroquinone; rapid addition of xylene or inverse addition result in very fine crystals which pass through Watman #1 filter paper, while slow xylene addition results in large readily filterable crystals. Large crystals are preferred.

Separation Step (F)

The crystal mass is preferably recovered by centrifugation. The centrate is 10 to 25 weight percent liquid, preferably 10 to 15 weight percent liquid.

Second Distillation Step (G)

Since the distribution coefficient for hydroquinone in MIBK/$H_2O$ favors MIBK by a factor of 3–5, the volume of MIBK (and xylene) has to be reduced sufficiently to counter the unfavorable distribution coefficient. The concentration of the bottoms stream from the second distillation is optimally conducted to the point where the hydroquinone content in the organic phase is negligible and the color body concentration in the aqueous phase is minimal. If concentration is stopped short of this point, significant losses of hydroquinone to the organic phase will occur. On the other hand, if concentration is allowed to proceed beyond this point, the concentration of color bodies in the aqueous phase is increased. In the extreme, the density of the organic phase nearly matches that of the aqueous phase and phase separation is difficult.

MIBK is an excellent solvent for hydroquinone and color bodies, while water is an excellent solvent for hydroquinone and a poor solvent for color bodies, and xylene is a poor solvent for both hydroquinone and color bodies. If rectification of MIBK/xylene occurs during distillation so that the ratio, in the pot, of xylene to MIBK is high, the distribution coefficient of color bodies in the mixed organic/$H_2O$ system decreases, forcing more color into the aqueous phase. In the present study, an MIBK/xylene weight ratio in the second distillation tower bottoms of 0.36 gave satisfactory results.

The concentration of hydroquinone in the aqueous phase at the end of the distillation also affects the distribution of color bodies. As the concentration of hydroquinone in the aqueous phase at the end of the concentration is increased from about 8 percent to about 12 percent, the amount of color bodies residing in the aqueous phase is increased. It is desirable, therefore, to add sufficient water to the distillation tower to give a hydroquinone concentration in the tower bottoms of about 8 percent. The amount of water fed to the second distillation column should be sufficient to both insure the transfer of most of the hydroquinone to the aqueous phase and to compensate for water lost in the overhead with any solvent/water azeotrope.

The ratio of organic to aqueous phase in the distillation bottoms is critical and depends on how pure the p-diisopropylbenzene dihydroperoxide reactor feed (step A) is. The purer the feed is the smaller may be the ratio because the organic phase would have to "hold" less tars. Generally the weight ratio is between 0.5:10 and 5:10 and preferably is about 1:10. A ratio of 1:10 gives a good balance between the goals of minimizing the flow of organic phase in the bottoms and allowing some flexibility in the operation of the distillation column.

Phase Separation Step (H)

The two-phase bottoms stream from the second distillation step is phase separated; the organic phase (containing over 95 percent of the color bodies and less than 1 percent of the hydroquinone) is fed directly to the tar removal column.

Repulping Step (M)

The mixture in the repulper is agitated and heated. At atmospheric pressure, maximum temperature in the repulper is about 55° C. If the repulper is pressurized, the temperature can be higher but not over 100° C. Heat may be furnished by any convenient source such as an external heat exchanger or a heating jacket on the repulper.

Crystallizer Step N)

The mixture in the crystallizer is cooled to from about 20° to about 25° C. at ambient pressure.

As an aid in understanding the process of this invention, the overall process will be described with reference to the flow diagram, with the proviso that this diagram is an exemplary embodiment of the invention and the process is not limited to this particular arrangement. For example, the solid liquid separation step (F) is shown as a centrifuge; however, this operation could be done by a filter. The symbols represent unit operations, and ancillary equipment such as heat exchangers, pumps, reflux drums and steam jet ejectors have not been illustrated. Also, secondary process streams (e.g. vapor leaving crystallizers) and utility streams (e.g. steam) have been omitted.

Referring to the drawing, the rearranger feed 1 contains p-diisopropylbenzene dihydroperoxide, reaction solvent and minor amounts of unreacted p-diisopropylbenzene (precursor to the dihydroperoxide) and impurities such as diisopropylbenzene monohydroperoxide and α-hydroxy-α'-hydroperoxy diisopropylbenzene. This feed is mixed in the rearranger reactor 3 with the acid catalyst 2 (such as sulfuric acid). Typical conditions for the rearrangement reaction are 180° F. (82° C.) and 0 to 20 pounds per square inch gauge pressure (0–138 kilopascals).

The rearranger effluent 4 is mixed in-line with anhydrous ammonia gas which enters via stream 5. The acid present in the reactor effluent is neutralized and this neutralized stream 7 enters the salt separator 8.

The salt separator 8 is a filter in which the acid salts are collected as a filter cake (stream 9). Rearranger effluent, free of salts, leaves the salt separator via stream 10. Stream 10 flows on to the distillation column 20. To the distillation column is also fed stream 108 which comprises the combination of the extract from step (K) (Extraction column III, item 83, stream 87) with the centrate from Centrifuge II, item 106, stream 107 (step 0). In this case, streams 10 and 108 are combined to form stream 11 before being fed to Distillation Column I (item 20).

The distillate (stream 25) consists of all of the acetone, most of the MIBK, and some xylene and water entering Distillation Column I in feed stream 11.

The bottoms stream (28) flows on to Precipitator 30 where precipitating solvent (e.g. xylene) enters via stream 29. The Precipitator is a vessel with sufficient holding capacity to permit the formation of the large hydroquinone crystals already discussed. Its contents are mildly agitated to keep the solid phase suspended.

The two-phase mixture (stream 31) exits the Precipitator and enters Centrifuge I (item 33) where it is separated into slurry 37 and centrate 34 (the liquid phase from Step F).

Centrate (34), containing about 25 percent of the hydroquinone and nearly all the color body or tar material from stream 28, is fed to Distillation Column II (item 47) which corresponds to step (G). The water feed is shown as stream 49 entering the bottom, but it may be added at one of the lower stages of the column, mixed with the feed stream 47, or it, may be added at both of these points. The distillation is carried out as described in the Summary Section, and the section on step (G) above so as to remove nearly all of the xylene precipitation solvent and most of the MIBK in the distillate 48. At the same time the hydroquinone is extracted into the aqueous phase and tars are concentrated in the organic phase in the distillation bottoms 50.

The two-phase bottoms stream 50 flows on to phase separator 51, which is a vessel designed to permit the decantation of the organic phase from the aqueous phase which contains the hydroquinone. The aqueous phase 52 is withdrawn and transferred to Extraction Column I (item 57) which corresponds to Step (I).

Stream 52 is purified by extraction with MIBK stream 60. The organic extract 59 is back extracted with water (stream 76) in Extraction Column II (item 70) in order to recover the hydroquinone extracted along with the tars in Extraction Column I. The raffinate from Extraction Column I (stream 61) and the extract from Extraction Column II (stream 79) are combined into stream 81.

The hydroquinone in stream 81 is extracted into MIBK (stream 84) in Extraction Column III (item 83), which corresponds to step (K). The hydroquinone-bearing extract 87 is recycled to Distillation Column I, as described above. The aqueous raffinate from Extraction column III (stream 85) is supplemented with make-up water (stream 77) and used as the water feed (stream 49) to Distillation Column II (item 47) and as the water extractant (stream 76) to Extraction Column II (item 70).

The wet crystals (stream 37) from Centrifuge I (item 33) are transferred to the repulper. Repulper 80 is an agitated vessel in which the wet hydroquinone crystals are dissolved in acetone which enters via stream 38. The mixture thus formed (comprised of hydroquinone, acetone, MIBK and xylene) is designated stream 42 and flows from the repulper to crystallizer 90, which corresponds to step (N).

A slurry of hydroquinone crystals in the solvent (principally acetone) 95 exits the Crystallizer 90 and flows on to Centrifuge II 106.

Centrifuge 106 separates the hydroquinone crystals 110 (this time wet with acetone) from the centrate 107 which is recycled to the distillation column 20. Following centrifugation, the wet hydroquinone crystals are conveyed to a drier for conventional handling thereafter.

The tar-containing organic phase 53, from phase separator 51, and the organic raffinate from Extraction Column II (item 70) are fed to Distillation Column III (item 73, the tar removal column). A concentrated tar stream exits that Distillation Column as bottoms stream 74, and the distillate (75) comprises MIBK, xylene, and a minor amount of water.

A better understanding of the present invention will be obtained from the following working example which is merely illustrative and not limitative of the present invention. Unless otherwise stated, percentages are by weight.

EXAMPLE

A feed mixture (stream 1) was made by combining 230 grams of p-diisopropylbenzene dihydroperoxide (p-DHP) cake with 615 grams of MIBK and 93 grams of acetone and warming to 60° C. The cake was obtained as the product of a process similar to that described in U.S. Pat. No. 3,883,600 (column 7, lines 9–13) and in *Chemical Engineering*, June 9, 1975, pages 50–51 (vacuum drum filter cake). The cake was comprised of 85.9 percent p-DHP, 12.9 percent α-hydroxy-α'-hydroperoxy diisopropylbenzene (p-HHP) and about 1.2 percent p-diisopropylbenzene. This was high quality feed, indicated by the high ratio of p-DHP to p-HHP (about 6.6). A feed-containing a higher p-HHP level (e.g. a ratio of 2.5 to 4.0) may result in higher color body formation. This, in turn, may influence the manner in which the purification scheme is operated, e.g. the extractors may have to be operated more rigorously, or designed somewhat larger.

Five milliliters of 50 percent $H_2O_2$ was added to the solution in order to convert any α-hydroxy-α'-hydroperoxy diisopropylbenzene and α,α'-dihydroxydiisopropylbenzene (both of which may be present in the cake) to hydroquinone. This technique is explained in British Pat. No. 910,735. It helps to improve the yield.

The rearrangement reaction was initiated by the rapid addition of this p-DHP feed to a nitrogen-purged, stirred flask containing 1.0 gram of concentrated $H_2SO_4$ in 80 grams of acetone. Two additional one gram aliquots of concentrated $H_2SO_4$ were added to the reaction flask after one-third and two-thirds of the p-DHP feed had been added. The temperature of the rearrangement was maintained at 60° to 70° C. by external cooling in an ice water bath. After all the feed was added, the rearranged solution was allowed to stand with stirring for an additional 10 minutes, neutralized with anhydrous $NH_3$ (stream 5) to a pH of 3.5 to 4.2 and vacuum filtered to remove the salts (stream 9).

To a filtered rearrangeate (stream 10) of a given run was added the acetone recrystallization centrate (stream 107) and the MIBK extract of Extractor II from the previous run (stream 87). The mixture (stream 11) was concentrated in vacuo to 38 percent hydroquinone. To the hot concentrate (stream 28) was added 200 grams of xylene (stream 29) with stirring. The solution was cooled to 20° C., at which point crude hydroquinone was recovered by centrifugation through Watman #1 paper. The crude hydroquinone cake (stream 37) was dissolved in sufficient acetone (DMK) at 50° C. to yield a solution 40 percent in hydroquinone. Cooling to 20° C. followed by a second centrifugation (step 0) and drying gave 64 grams of hydroquinone. The centrate (stream 107) was retained for addition to rearrangeate of the following run.

Centrate (stream 34) from the crude hydroquinone centrifuge (item 33, step F) was combined with recycled aqueous raffinate (stream 85 or 49) of Extraction Column III. This was the feed to Distillation Column II (item 47, step G). The feed was distilled through a 12 inch vigreux column at ambient pressure until about 30 grams of organic phase remained in the pot. Both solvents distilled as their water azeotropes, stream 48 (MIBK/$H_2O$ BP 87.9°, m-xylene/$H_2O$ BP 92°).

The contents of the pot were phase separated at 70°–75° C. The organic phase (stream 53) was discarded and the aqueous phase (stream 52) was extracted (Extraction Column I) with a minimal amount of MIBK (stream 60) at 80° C. The MIBK extract (stream 59) was back extracted (Extraction Column II) at 80° C. with four equal weights of water (stream 76). The MIBK raffinate (stream 71) was discarded while the aqueous extract (stream 79) was combined with the aqueous raffinate from Extraction Column I (stream 61).

This combined stream (81) generally contains about 85 to 95 percent of the hydroquinone in the purification loop (steps G–L). This hydroquinone was recovered for recycle to the concentrator by extraction into MIBK in Extraction Column III (step K, item 83). The mixture was extracted with two 115 gram portions of MIBK (stream 84). The MIBK extract (stream 87) was retained for addition to the rearrangeate of the subsequent run, while the aqueous raffinate (stream 85), depleted of hydroquinone, was retained for addition to the crude hydroquinone centrate (stream 34) and to Extraction Column II in the following run.

Table 1 lists composition data for all streams within the recommended process. The weights of components have been adjusted to 100 percent material balance. This adjustment was necessary to compensate for material removed during sampling and that lost in transferring material during processing. Raw analytical data used to calculate the data in Table 1 are given in Table 2.

Table 1

Material Balanced Stream Compositions for Drawing and Example

| Stream No. | HQ | $H_2O$ | DMK* | MIBK | Xylene | Others | Total |
|---|---|---|---|---|---|---|---|
| 10 | 92.4 | 7.8 | 229.9 | 655.0 | | | 985.1 |
| 107 | 12.9 | 0.1 | 134.6 | 9.7 | 11.8 | 0.5 | 169.6 |
| 87 | 22.4 | 8.7 | | 230.8 | | 1.0 | 262.9 |
| 11 | 127.7 | 16.6 | 364.5 | 895.5 | 11.8 | 1.5 | 1417.6 |
| 28 | 127.7 | 0.9 | | 178.6 | | 9.0 | 316.2 |
| 29 | | | | | 216.0 | | 216.0 |
| 31 | 127.7 | 0.9 | | 178.6 | 216.0 | 9.0 | 532.2 |
| 24 | 25.2 | 0.8 | | 167.3 | 202.3 | 8.4 | 404.0 |
| 37 | 102.5 | 0.1 | | 11.3 | 13.7 | 0.6 | 128.2 |
| 25 | | 15.7 | 364.5 | 709.4 | 11.8 | | 1101.4 |
| 85 | 2.0 | 477.0 | | 7.2 | | | 486.2 |
| 77 | | 164.2 | | | | | 164.2 |
| 49 | 2.0 | 465.0 | | 7.2 | | | 474.2 |
| 50 | 27.2 | 315.1 | | 3.1 | 8.7 | 12.7 | 366.8 |
| 48 | | 150.7 | | 167.1 | 193.6 | | 511.4 |
| 52 | 26.4 | 314.4 | | | | | 340.8 |
| 75 | | 2.1 | | 36.2 | 8.7 | | 47.0 |
| 74 | | 2.8 | | | | 16.2 | 19.0 |
| 60 | | | | 40.0 | | | 40.0 |
| 59 | 8.3 | 6.7 | | 34.8 | | | 49.8 |
| 61 | 18.1 | 307.7 | | 5.2 | | | 331.0 |
| 76 | | 176.2 | | | | | 176.2 |
| 71 | 2.0 | 1.4 | | 33.1 | | 3.5 | 40.0 |
| 79 | 6.3 | 178.0 | | 1.7 | | | 186.0 |
| 81 | 24.4 | 485.7 | | 6.9 | | | 517.0 |

Table 1-continued

Material Balanced Stream Compositions for Drawing and Example

| Stream No. | HQ | H$_2$O | DMK* | MIBK | Xylene | Others | Total |
|---|---|---|---|---|---|---|---|
| 84 | | | | 232.1 | | | 232.1 |
| 108 | 35.3 | 8.8 | 134.6 | 240.5 | 11.8 | 0.5 | 432.5 |
| 38 | | | 153.8 | | | | 153.8 |
| 42 | 102.5 | 0.1 | 153.8 | 11.3 | 13.7 | 0.6 | 282.0 |
| 95 | 102.5 | 0.1 | 153.8 | 11.3 | 13.7 | 0.6 | 282.0 |
| 110 | 89.6 | | 19.2 | 1.4 | 1.7 | 0.1 | 112.0 |
| 53 | 0.8 | 0.7 | | 3.1 | 8.7 | 12.7 | 26.0 |

*Acetone, dimethyl ketone

Table 2

Analytical Data for Stream Compositions for the Example

| Stream No. | HQ | H$_2$O | DMK | MIBK | Xylene | Others | Total |
|---|---|---|---|---|---|---|---|
| 10 | 88.3 | 7.8 | 229.9 | 655 | | | 970 |
| 87 | 21.1 | 8.7 | | 230.8 | | | 265 |
| 11 | 127 | 25.8 | 341 | 1140 | | | 1610 |
| 28 | | | | | | | 333 |
| 29 | | | | | 200 | | 200 |
| 31 | | | | | 200 | | 533 |
| 34 | 28.1 | 0.8 | | 167.3 | 202.3 | 8.4 | 407 |
| 37 | 102.5 | | | | | | 109.7 |
| 85 | 2.0 | 439.8 | | 7.2 | | | 449 |
| 49 | 1.6 | 363.4 | | | | | 365 |
| 50 | 27.4 | 315.1 | | 3.1 | 8.7 | | 367 |
| 53 | 0.8 | 0.7 | | 3.1 | 8.7 | 12.6 | 26 |
| 52 | 26.6 | 314.4 | | | | | 341 |
| 60 | | | | 40 | | | 40 |
| 59 | 8.5 | 3.9 | | 32.9 | | 4.7 | 50 |
| 61 | 17.8 | 300 | | 5.2 | | | 323 |
| 76 | 0.8 | 169.2 | | | | | 170 |
| 71 | 2.2 | 1.4 | | 26.9 | | 3.5 | 30.5 |
| 79 | 5.7 | 165.6 | | 1.7 | | | 173 |
| 81 | 23.5 | 465.6 | | 6.9 | | | 496 |
| 84 | | | | 230 | | | 230 |

One measurement of hydroquinone purity is color number. Color number is an arbitrary color measurement obtained by comparing a 5 percent hydroquinone solution in a dilute acetic acid with a known set of color standards. The color standard is a platinum/cobalt (Pt/Co) standard of the American Public Health Association (APHA). A standard color number curve is plotted using various solutions of the standard. As furnished, the standard has a color number of 500. A one percent solution would then have a color number of 5, etc. Measurements of light absorbance are made on an instrument such as a Beckman Spectrophotometer at a wave length of 390. For hydroquinone, a color number of less than or equal to 20 corresponds to commercially available photograde hydroquinone and meets the ASA specification for color and acetone solubility.

The crude hydroquinone centrifuge cake (stream 37) was recrystallized from acetone in about 80 percent yield in the experimental work on which the example is based. Samples of this recrystallized material were generally greater than 99 weight percent hydroquinone and had a (Pt/Co) color number of about 35, which indicates high quality technical grade material.

Other embodiments of this invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. In a process for making and recovering hydroquinone comprising the steps of:

(A) reacting a feed stream comprising p-diisopropyl-benzenedihydroperoxide
  (1) in a reaction solvent selected from the group consisting of methyl isopropyl ketone, diisopropyl ketone, methyl isobutyl ketone, cyclohexanone, 1-pentanol, 3-pentanol, diethyl ether, diisopropyl ether, ethylisopropyl ether and mixtures of the foregoing with acetone;
  (2) with an acid catalyst selected from the group consisting of $H_3PO_4$, $HClO_4$, p-toluene-sulfonic acid, $SO_2$, $HBF_4$, $H_2SiF_6$, $BF_3$ and any other Lewis acid in a concentration of from 0.05 to 3.0 weight percent of the reaction mixture;
  (3) with less than 3 weight percent water present in the reaction mixture;
  (4) within a temperature range of from 50° to 100° C. to form hydroquinone and acetone;
(B) adjusting the pH of the mixture to from about 2.5 to 5.5 after the reaction by adding a base selected from the group consisting of anhydrous ammonia, methylamines, triethylamines, and alkali and alkaline earth metal hydroxides, carbonates and oxides, thereby causing salts to form and precipitate; and
(C) separating the precipitated salts from the supernatant mixture;
(D) feeding the supernatant mixture to a first distillation column in which most of the more volatile components are stripped out in the distillate and a concentrated hydroquinone stream is removed as tower bottoms; the improvement which comprises the steps of:
(E) precipitating hydroquinone crystals by adding a precipitating solvent to the bottoms stream from step (D);
(F) separating the hydroquinone crystals in the slurry obtained in step (E) from the supernatant organic liquid;
(G) feeding the supernatant liquid from step (F) to a second distillation column in which are combined the unit operations of distillation, to remove the acetone and most of the reaction solvent in the distillate, and extraction of the hydroquinone into a water phase which exits the second distillation column together with an organic phase as the distillation bottoms stream;
(H) subjecting the bottoms from step (G) to a phase separation wherein the aqueous phase contains most of the hydroquinone and the organic phase contains substantially all the impurities and a small quantity of hydroquinone;
(I) extracting the aqueous phase from step (H) with an extractant selected from the group consisting of methyl isopropyl ketone, diisopropyl ketone, methyl isobutyl ketone, cyclohexanone, 1-pentanol, 3-pentanol, diethyl ether, diisopropyl ether and mixtures of the foregoing in order to remove tars;
(J) extracting the organic extract from step (I) with water in order to recover residual hydroquinone from said extract;
(K) combining the aqueous raffinate from step (I) with the aqueous extract from step (J) and extracting the combined stream with an extractant selected from the group consisting of methyl isopropyl ketone, diisopropyl ketone, methyl isobutyl ketone, cyclohexanone, 1-pentanol, 3-pentanol, diethyl ether, diisopropyl ether, ethylisopropyl ether and mixtures of the foregoing; and (L) recycling the organic extract from step (K) to the distillation step (D).

2. The process improvement as recited in claim 1 which further comprises the steps of:
- (M) Repulping the hydroquinone from step (F) in acetone;
- (N) crystallizing the hydroquinone from the acetone; and
- (O) separating the hydroquinone crystals from the supernatant liquid.

3. The process improvement of claim 2 further comprising the steps of:
- (P) feeding the organic phase from step (H) and the organic raffinate from step (J) to a distillation column which separates a heavy bottoms stream from the lighter solvents.

4. The process improvement of claim 3 wherein the water extractant for steps (G) and (J) is obtained by recycling the aqueous raffinate from step (K) with the addition of sufficient fresh water to make the material balance.

5. The process improvement of claim 4 in which the supernatant liquid from step (O) is recycled to step (D).

6. The process improvement as recited in claim 4 wherein methyl isobutyl ketone is the reaction solvent and the extractant in steps (I) and (K); the feed to step (A) comprises a solution of about 20–22 weight percent diisopropylbenzene dihydroperoxide (p-DHP) in MIBK containing about 10 weight percent acetone; sulfuric acid is the catalyst in step (A); reaction temperature in step (A) is from about 65° to about 70° C.; less than 1 weight percent water is present in the reaction mixture; and wherein the pH is adjusted to from 3 to 4 with anhydrous ammonia in step (B).

7. The process improvement of claim 6 wherein:
- (a) the concentration of hydroquinone in the distillation bottoms from step (D) is from about 30 to 45 weight percent;
- (b) the precipitating solvent for step (E) is xylene;
- (c) the weight ratio of xylene added in step (E) to the distillation bottoms from step (D) is from 0.1 to 1.5;
- (d) step (F) is accomplished by centrifugation;
- (e) the concentration of hydroquinone in the aqueous phase of the bottoms stream from step (G) is about 8 to 10 weight percent;
- (f) the weight ratio of organic to aqueous phase in the bottoms stream from step (G) is between 0.5:10 and 5:10 and
- (g) the concentration of hydroquinone in the mixture leaving repulping step (M) is between 30 and 50 weight percent.

8. The process improvement of claim 7 wherein:
- (a) the distillation bottoms stream from step (D) entering the precipitator is cooled to about 25° C.;
- (b) the weight ratio of xylene added in step (E) to the distillation bottoms from step (D) is about 0.6
- (c) the centrate from step (F) is 10 to 25 weight percent liquid;
- (d) the concentration of hydroquinone in the aqueous phase of the bottoms stream from ste (G) is about 8 weight percent; and
- (e) the weight ratio of organic to aqueous phase in the bottoms stream from step (G) is about 1:10.

9. The process improvement of claim 8 wherein:
- (a) the reactor feed stream contains α-hydroxy-α'-hydroperoxy diisopropylbenzene (p-HHP);
- (b) the weight ratio of p-DHP to p-HHP is about 6.6; and
- (c) $H_2O_2$ is added to the reaction step (A) to improve the yield.

* * * * *